United States Patent
Fahrenholtz et al.

(10) Patent No.: US 10,322,208 B2
(45) Date of Patent: Jun. 18, 2019

(54) SURFACE COATING METHOD TO IMPROVE IMPLANTABLE DEVICE BIOCOMPATIBILITY

(71) Applicant: William Marsh Rice University, Houston, TX (US)

(72) Inventors: Monica Fahrenholtz, Houston, TX (US); Kathryn Jane Grande-Allen, Houston, TX (US)

(73) Assignee: WILLIAM MARSH RICE UNIVERSITY, Houston, TX (US)

( * ) Notice: Subject to any disclaimer, the term of this patent is extended or adjusted under 35 U.S.C. 154(b) by 0 days.

(21) Appl. No.: 15/579,079

(22) PCT Filed: Jun. 1, 2016

(86) PCT No.: PCT/US2016/035267
§ 371 (c)(1),
(2) Date: Dec. 1, 2017

(87) PCT Pub. No.: WO2016/196633
PCT Pub. Date: Dec. 8, 2016

(65) Prior Publication Data
US 2018/0169300 A1 Jun. 21, 2018

Related U.S. Application Data

(60) Provisional application No. 62/169,374, filed on Jun. 1, 2015.

(51) Int. Cl.
*A61L 31/10* (2006.01)
*A61L 27/34* (2006.01)
(Continued)

(52) U.S. Cl.
CPC ............. *A61L 27/34* (2013.01); *A61L 27/507* (2013.01); *A61L 27/52* (2013.01); *A61L 27/54* (2013.01);
(Continued)

(58) Field of Classification Search
CPC .......... A61L 27/34; A61L 31/10; A61L 31/16; A61L 2300/252; A61L 2300/256;
(Continued)

(56) References Cited

U.S. PATENT DOCUMENTS 8,100,963 B2 * 1/2012 Roth ..................... A61F 2/91
606/198
2004/0093080 A1 5/2004 Helmus et al.
(Continued)

OTHER PUBLICATIONS (PCT/Rule 44.1); International Search Report; pp. 1-13; dated Sep. 2016.

*Primary Examiner* — Ernst V Arnold
(74) *Attorney, Agent, or Firm* — Fletcher Yoder, P.C.

(57) ABSTRACT

Techniques for modifying the surface of implantable devices, such as bioprosthetic valves, to improve the biocompatibility of the implantable devices are provided. In particular, a customizable, non-fouling surface coating may be formed on the surface of implantable devices that improves the biocompatibility of the implantable devices and has the potential to further reduce the occurrence of complications for patients of all ages. Additionally, various molecules of interest to specifically promote endothelialization of the implantable device may be added to the surface coating, which may facilitate the formation of an endothelial layer on the surface of the implantable device that would naturally maintain a non-thrombogenic, non-immunogenic environment in the long-term.

11 Claims, 3 Drawing Sheets

(51) Int. Cl.
  *A61L 27/54* (2006.01)
  *A61L 31/16* (2006.01)
  *A61L 27/50* (2006.01)
  *A61L 27/52* (2006.01)
  *A61L 31/14* (2006.01)

(52) U.S. Cl.
  CPC ............. *A61L 31/10* (2013.01); *A61L 31/145* (2013.01); *A61L 31/16* (2013.01); *A61L 2300/252* (2013.01); *A61L 2300/256* (2013.01); *A61L 2400/18* (2013.01); *A61L 2420/02* (2013.01); *A61L 2420/08* (2013.01); *A61L 2430/20* (2013.01)

(58) Field of Classification Search
  CPC ............. A61L 2400/18; A61L 2420/02; A61L 2420/08; A61L 2430/20; A61L 27/507; A61L 27/52; A61L 27/54; A61L 31/145; C08L 71/02
  See application file for complete search history.

(56) References Cited

U.S. PATENT DOCUMENTS

| | | |
|---|---|---|
| 2005/0165128 A1 | 7/2005 | Cohn et al. |
| 2006/0034884 A1 | 2/2006 | Stenzel |
| 2007/0042017 A1* | 2/2007 | Kutryk .................... A61L 27/08 424/423 |
| 2007/0071926 A1 | 3/2007 | Rypacek et al. |
| 2007/0254006 A1 | 11/2007 | Loose et al. |
| 2009/0264538 A1 | 10/2009 | Hubbell et al. |
| 2011/0052788 A1 | 3/2011 | Messersmith et al. |

* cited by examiner

SURFACE COATING METHOD TO IMPROVE IMPLANTABLE DEVICE BIOCOMPATIBILITY

CROSS-REFERENCE TO RELATED APPLICATIONS

This application claims priority to and the benefit of U.S. Provisional Application No. 62/169,374, entitled "SURFACE COATING METHOD TO IMPROVE IMPLANTABLE DEVICE BIOCOMPATIBILITY," filed Jun. 1, 2015, and PCT Application No. PCT/US16/35267, entitled "SURFACE COATING METHOD TO IMPROVE IMPLANTABLE DEVICE BIOCOMPATIBILITY," filed Jun. 1, 2016, which are herein incorporated by reference in its entirety for all purposes.

BACKGROUND

The present disclosure relates generally to biocompatible surface coatings for implantable devices, such as bioprosthetic heart valves.

Each year, over 90,000 prosthetic valves are implanted in the United States, and 280,000 are implanted worldwide, about half of which are bioprosthetic valves. Bioprosthetic valves may be formed from valves of animals or other animal tissue, which is also called xenogeneic tissue. The outcome of patients undergoing bioprosthetic valve replacement may be affected by the valve biocompatibility, such as the valve hemodynamics and thrombogenicity. In some cases, surfaces of bioprosthetic valves may be modified to improve biocompatibility by reducing or eliminating interactions between blood components, such as cells, proteins, platelets, and the like, and the xenogeneic tissue of the bioprosthetic valves. The improved biocompatibility of bioprosthetic valves may reduce the occurrence of complications and improve outcomes for patients all ages receiving valve replacements.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

The present disclosure describes techniques for modifying the surface of implantable devices, such as bioprosthetic valves, to improve the biocompatibility of the implantable devices. In particular, the present approaches create a customizable, non-fouling surface coating on the surface of implantable devices that improves the biocompatibility of the implantable devices and has the potential to reduce the occurrence of complications for patients of all ages. Additionally, various molecules of interest to specifically promote endothelialization of the implantable device may be added to the surface coating, which may facilitate the formation of an endothelial layer on the surface of the implantable device that would naturally maintain a non-thrombogenic, non-immunogenic environment in the long-term.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The disclosed embodiments relate to a process for chemically modifying the surface of an implantable device to improve its biocompatibility by reducing or eliminating interactions between blood components, such as cells, proteins, platelets, and the like, and the material or materials of the implantable device. Additionally, the surface modification can be designed to encourage endothelial cell or endothelial progenitor cell colonization of the surface of the implantable device for long-term compatibility. As will be described in more detail below, the process for chemically modifying the surface of an implantable device creates a customizable, non-fouling surface coating on the surface of the implantable device that has the potential to reduce the occurrence of complications and improve patient outcomes. Additionally, various molecules of interest may be added to the surface coating, such as molecules of interest that may specifically promote endothelialization on the surface of the implantable device. This pro-endothelial coating would reduce, minimize, or prevent unwanted interactions with blood cells and proteins, and if an endothelial layer eventually forms on the surface of the implantable device, the endothelial lining would naturally maintain a non-thrombogenic, non-immunogenic environment in the long-term. While the embodiments described below relate to bioprosthetic heart valves (e.g., commercially available bioprosthetic heart valves), it should be noted that the present techniques may be applied to any implantable device, such as other bioprosthetic valves, vascular grafts, vascular stents, other types of blood-contacting devices, or any implantable biological or synthetic material containing amine groups.

Figure 1:
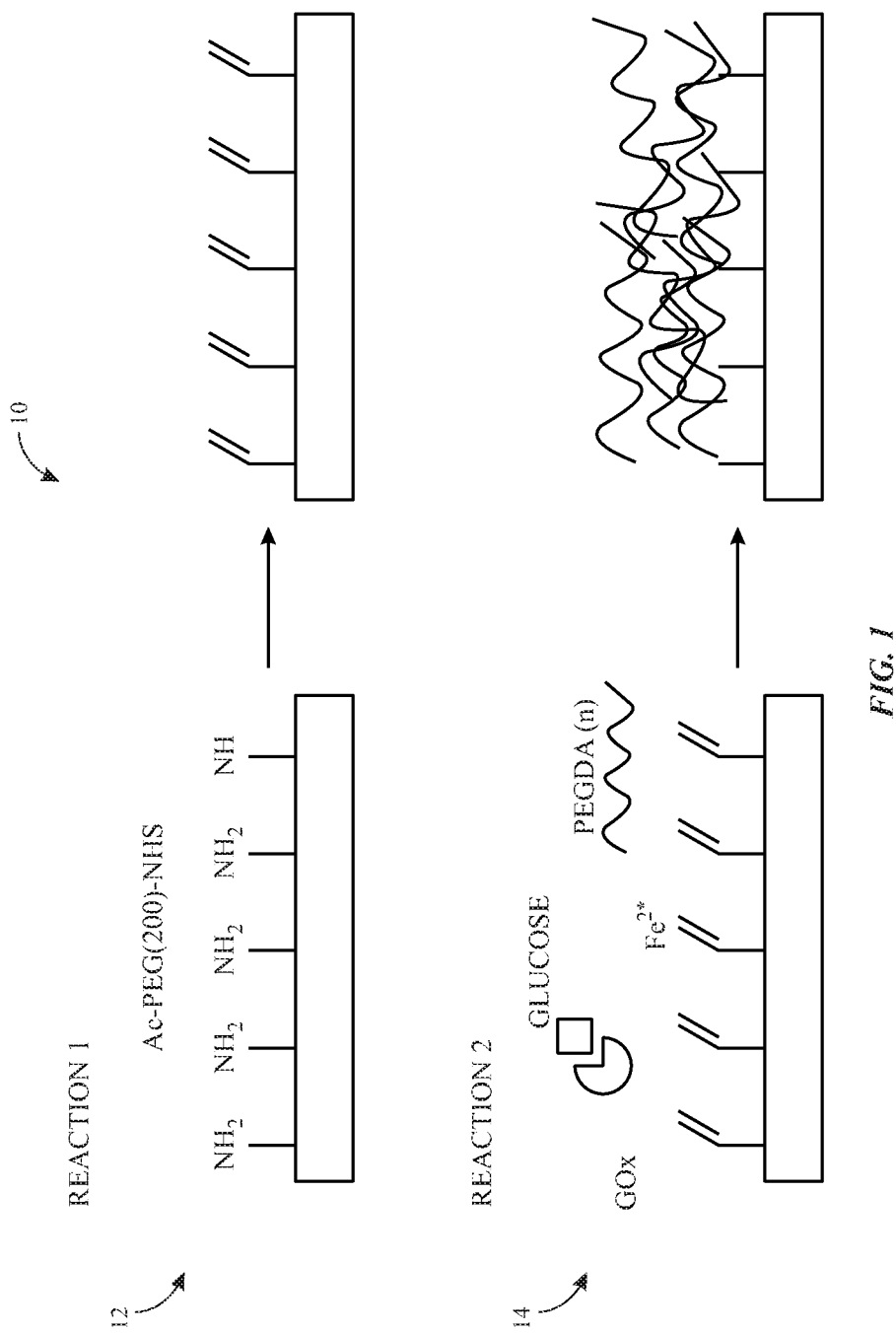
FIG. 1 illustrates a schematic diagram of an embodiment of a two-step surface coating method for coating a bioprosthetic valve.

FIG. 1 illustrates a schematic diagram of an embodiment of a two-step surface coating method 10 (e.g., a two-step reaction) to create a customizable, non-fouling, polyethylene-glycol (PEG)-based, thin hydrogel coating on the surface of biological tissues. PEG is an advantageous material for this purpose because it not only has well-characterized anti-fouling properties, but it is already FDA-approved for use in blood-contacting materials, e.g., as a conjugate for intravenous drugs. Biological tissues are rich in amine groups, which are excellent targets for surface modification chemistries. The first step 12 (e.g., first reaction) of the two-step surface coating method 10 takes advantage of the reactive amine groups on the surface of bioprosthetic tissue valves to add heterobifunctional linker molecules (e.g., "anchoring points") via an N-hydroxysuccinimide ester (e.g., NHS) reaction with amine groups. As illustrated, in some embodiments, the heterobifunctional anchoring linker (e.g., a bifunctional PEG macromer) may include the amine-reactive NHS ester on one end, a short (e.g., approximately 2 kilo daltons (kDa)) PEG chain, and an acrylate group on the other end. In certain embodiments, the heterobifunctional linker (e.g., a bifunctional PEG macromer) may include the amine-reactive NHS ester on one end, the short PEG chain, and a thiol group on the other end. The heterobifunctional linker transforms the reactive amine group on the bioprosthetic valve tissue into an even more reactive acrylate group or thiol group suitable for hydrogel cross-linking. The short PEG linker also provides additional degrees of freedom to the acrylate group or the thiol group at the end, making it easier to link to the hydrogel coating in the second reaction. In coincidence with the first reaction stage, glucose is allowed to soak into the bioprosthetic valve tissue to set up the reaction conditions for the second reaction.

In the second step 14 (e.g., second reaction), the bioprosthetic valve tissue, now decorated with acrylate or thiol anchor points at the end of PEG chains, is submerged in a polyethylene diacrylate (PEGDA)-based solution with glucose oxidase and iron(II) sulfate. Glucose absorbed by the tissue during the first reaction diffuses out of the tissue, forming a locally high concentration at the tissue surface. This high concentration of glucose reacts with the glucose oxidase in the reaction solution to generate free radicals and initiate free radical polymerization of PEGDA. In particular, glucose reacts with the glucose oxidase in the reaction solution to form hydrogen peroxide. Hydrogen peroxide then undergoes a redox reaction with iron(II) sulfate to generate hydroxyl and hydroperoxyl radicals close to the tissue surface. These radicals then initialize the polymerization of PEGDA with the surface acrylate or thiol anchor points. Additional materials (e.g., peptides, proteins, aptamers, and/or antibodies) can be added to the surface during this reaction. For example, additional materials containing acrylate groups or thiol groups to facilitate a thiol-ene reaction may be added to the surface. This two-step surface coating method 10 will result in a thin (e.g., less than or equal to 100 micrometers (μm), 50 μm, 40 μm, 30 μm, 20 μm, 15 μm, or 10 μm), covalently attached coating of polymer and additive on the surface of the bioprosthetic valve. The PEG base of the hydrogel coating forms a "blank slate" due to its well-defined anti-fouling properties, to which various molecules of interest can be added to encourage endothelialization of the surface by native endothelial cells and endothelial progenitors, while discouraging unwanted interactions with blood components. The thin coating may not significantly change the surface or bulk mechanical properties of the bioprosthetic valve, thus preserving its primary function. This two-step surface coating method 10 can be added to the current bioprosthetic heart valve production process to produce coated bioprosthetic valves in commercially useful quantities.

In certain embodiments, the surface of bioprosthetic valves may be modified by submerging the bioprosthetic valve in a solution including PEG. For example, in some embodiments, the bioprosthetic valve may be submerged in 3 millimolar (mM) heterobifunctional PEG-n-hydroxysuccinimidyl-polyethylene glycol-acrylate in phosphate buffered saline (PBS, pH 7.4) with 5 grams per liter (g/L) glucose (e.g., the NHS-PEG-Acrylate solution). In certain embodiments, the bioprosthetic valve may be submerged in heterobifunctional PEG-n-hydroxysuccinimidyl-polyethylene glycol-thiol in PBS with 5 grams per liter (g/L) glucose (e.g., the NHS-PEG-Thiol solution). Additionally, in some embodiments, the bioprosthetic valve may be incubated in the NHS-PEG-Acrylate solution or the NHS-PEG-Thiol solution for at least 16 hours at room temperature. After incubation, the bioprosthetic valve may be removed from the NHS-PEG-Acrylate solution or the NHS-PEG-Thiol solution. In certain embodiments, the bioprosthetic valve may be washed after it is removed from the NHS-PEG-Acrylate solution or the NHS-PEG-Thiol solution. For example, the bioprosthetic valve may be washed in PBS any suitable number of times for any suitable period of time, such as, for example, three times for 10 minutes each.

Further, the bioprosthetic valve may be submerged in a coating solution, which may include 20 wt %, 6 kDa polyethylene glycol diacrylate (PEGDA), 5.93 μM glucose oxidase, and 4.744 mM iron (II) sulfate heptahydrate. The bioprosthetic valve may be submerged in the coating solution for any suitable amount of time to achieve a coating on the surface of the bioprosthetic valve with a desired thickness. For example, in some embodiments, the bioprosthetic valve may be submerged in the coating solution for approximately two minutes or for a time sufficient to form a consistent, approximately 8 μm thick coating on the surface of the bioprosthetic valve. Further, in certain embodiments, various molecules of interest to promote endothelialization, such as peptides, proteins, aptamers, and/or antibodies, may be added while the bioprosthetic valve is submerged in the coating solution. Finally, the bioprosthetic valve may be washed (e.g., in PBS) to stop the reaction and may be rinsed thoroughly to remove any remaining reactants.

In other embodiments, the coating solution may include polyethylene glycol diacrylamide (PEGDAA) instead of PEGDA. PEGDA may be subject to hydrolysis in vivo and, as a result, may degrade over time. PEGDAA is non-degradable, so it may be desirable to use PEGDAA in the coating solution for certain embodiments. PEGDAA has been shown to have the same reactivity and properties as PEGDA and thus, should provide a suitable substitute for PEGDA.

Additionally, variations of the NHS reactive group on the NHS-PEG-acrylate linker or the NHS-PEG-thiol linker may be used. NHS-ester is a broad class of amine-reactive compounds, which include variations such as succinimidyl carboxy methyl (SCM) ester and succinimidyl succinate (SS) ester, each with slightly different reactivities toward primary and secondary amines and susceptibility to hydrolysis in aqueous solution.

Further, in other embodiments, hydrogen peroxide may be reacted with other sources of iron(II) ions, instead of iron(II) sulfate, to generate hydroxyl and hydroperoxyl radicals close to the tissue surface. Indeed, any suitable source of iron(II) ions may be used. For example, in some embodiments, iron(II) phosphate, iron(II) ethylenediaminetetraacetic acid (EDTA), or any other ferrous salts may be used.

Additionally, in other embodiments, other peroxide-generating enzyme and substrate pairs may be used instead of glucose oxidase. For example, other peroxide-generating enzymes, such as those associated with fatty acid and alcohol breakdown in the body, as well as other radical-generating chemical reactions, may be used. However, glucose oxidase may be desirable to use, because glucose oxidase is naturally occurring, has non-toxic reaction products, and is easily produced in commercial quantities.

As noted above, the reaction time for the second reaction (i.e., the reaction of the bioprosthetic valve having the acrylate or thiol anchor points at the end of PEG chains with the coating solution) may be adjusted to achieve a desired thickness of the coating on the surface of the bioprosthetic valve. Additionally, in some embodiments, the molecular weight of PEGDA, or PEGDAA if used, may be adjusted to modulate the thickness of the coating. Further, in some embodiments, the concentration of glucose oxidase may be adjusted to achieve a desired thickness and/or surface coating area of the coating on the surface of the bioprosthetic valve. For example, increasing the glucose oxidase concentration may increase the surface coating area of the coating. Previous studies have shown a significant link between cell behavior and substrate stiffness, and it is well known that bioprosthetic heart valve tissue is significantly stiffer than native tissue. A thicker coating may mask the increased stiffness of the underlying tissue of the bioprosthetic valve on a local scale, such that cells colonizing the surface are unaffected by the underlying tissue mechanics, but the bulk mechanical properties necessary for valve function remain constant.

Further, in some embodiments, molecules of interest may be added to the coating on the surface of the bioprosthetic valve. In particular, it may be desirable to add molecules that promote endothelialization of the surface. For example, such molecules may include aptamers, antibodies, and designer collagen molecules capable of specifically attracting and supporting endothelial cells and endothelial progenitors without significantly interacting with other blood components.

Figure 2:
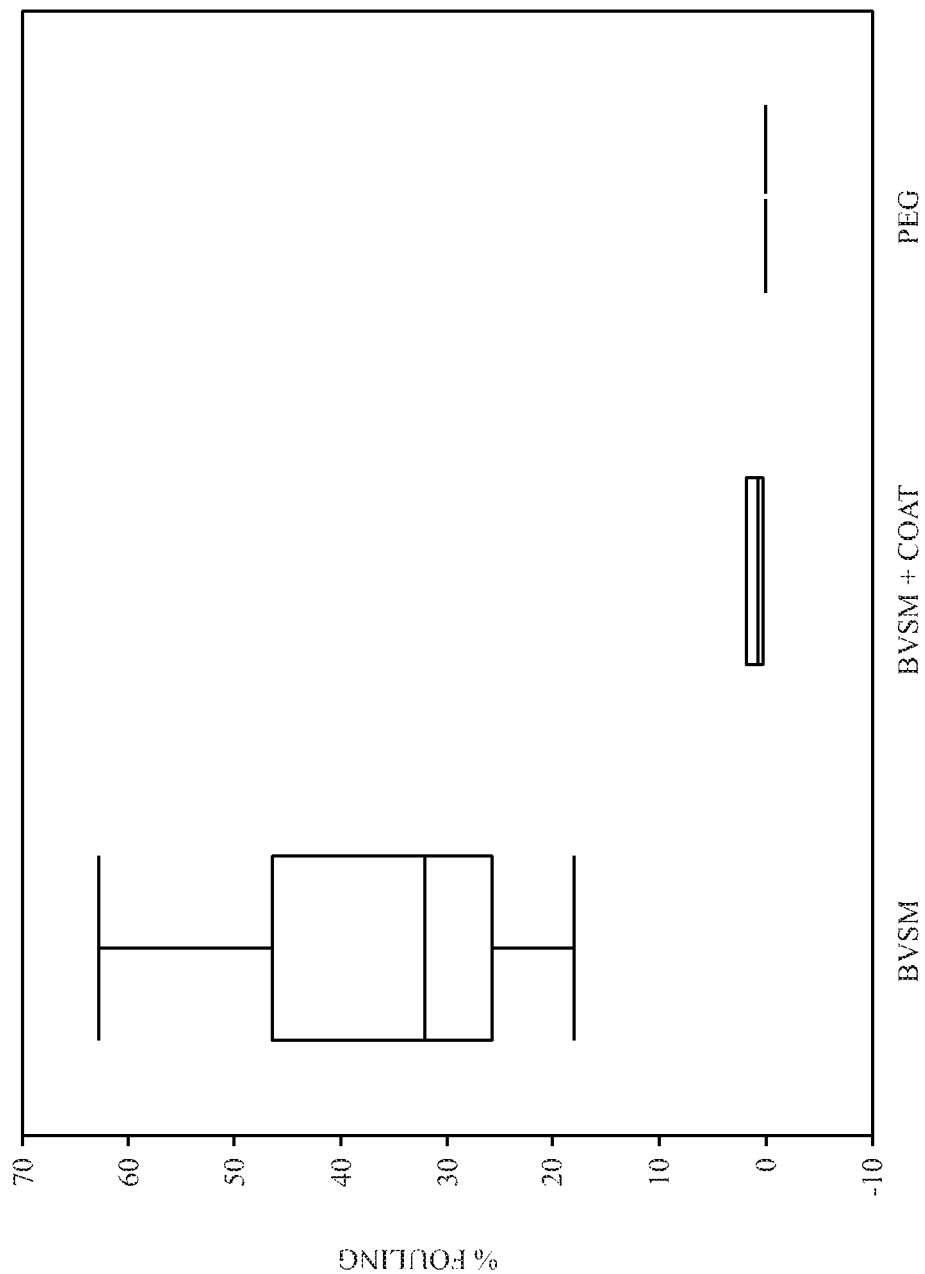
FIG. 2 illustrates the percentage of fouling for an uncoated bioprosthetic valve surface model (BVSM), a coated BVSM, and PEGDA-only hydrogel surface after rhodamine-conjugated bovine serum albumin was allowed to adsorb.

FIG. 2 shows the percentage of fouling of an uncoated bioprosthetic valve surface model (BVSM), a BVSM having the disclosed coating, and a PEGDA-only hydrogel surface after rhodamine-conjugated bovine serum albumin was allowed to adsorb to each surface. Significant deposition of protein (mean=36% surface area coverage) was observed on the BVSM surface, as compared to the coated BVSM and the PEGDA-only control, which showed no significant fouling (mean=0.85% and 0.02%, respectively), where a significant change is defined $p<0.0001$. As such, coating of the BVSM surface significantly reduced protein fouling, providing evidence that this surface coating can successfully prevent unwanted blood component-tissue interactions which lead to complications. In some embodiments, the percentage of fouling of a coated bioprosthetic valve may be at least five times or ten times less than the percentage of fouling of an uncoated bioprosthetic valve.

Figure 3:
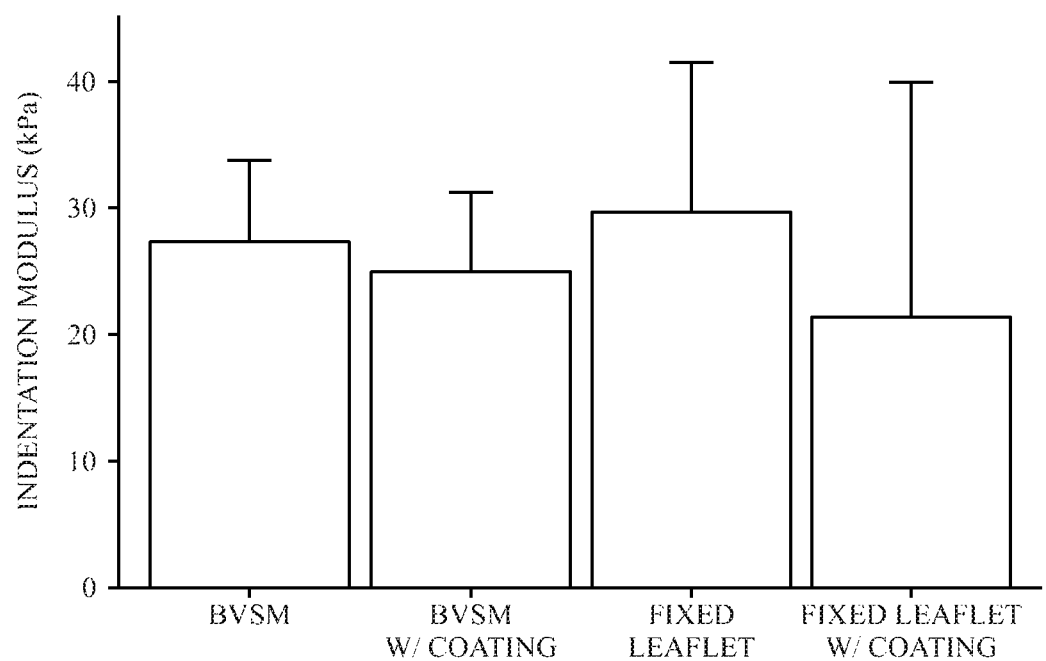
FIG. 3 illustrates the indentation modulus of an uncoated BVSM, a coated BVSM, an uncoated bioprosthetic tissue sample, and a coated bioprosthetic tissue sample after a bioindentation test.

FIG. 3 shows the indentation modulus in kilopascals (kPa) of an uncoated BVSM, a coated BVSM, an uncoated bioprosthetic valve tissue sample (e.g., an uncoated fixed leaflet), and a coated bioprosthetic valve tissue sample (e.g., a coated fixed leaflet) after a bioindentation test. In particular, the bioindentation test was implemented using a bioindenter having a 200 µm conical indentation tip with a constant loading rate up to a maximum load of 100 micronewtons (µN). The indentation modulus may be indicative of the material properties of the tissue surface, such as the stiffness. Altering the mechanical properties of the tissue surface, such as the stiffness, may have downstream effects on cells colonizing the tissue surface due to changes in the microenvironment. For example, altering the stiffness of the tissue surface may hinder the adhesion and function of endothelial cells and endothelial progenitors. As illustrated in FIG. 3, no significant difference in the indentation modulus (e.g., stiffness) was observed between coated and uncoated BVSMs or between coated and uncoated bioprosthetic valve tissue samples. As such, the surface coating does not appear to significantly alter the mechanical properties of the tissue surface and thus, may not significantly alter the adhesion and function of endothelial cells and endothelial progenitors on the tissue surface as compared to uncoated tissue surfaces.

As discussed herein, a customizable, non-fouling coating may be formed on surface of implantable devices, such as bioprosthetic valves. The customizable, non-fouling coating may be produced using a novel combination of reactions. One advantage of this method is that it does not change the current processing method, but instead is an add-on that can be seamlessly integrated with the current process, expediting commercialization. Additionally, neither reaction step in the process contains toxic components or organic solvents, and both can be carried out under mild conditions (22-25° C., pH 7.3-7.4), all of which reduce the need for stringent downstream washing, prevent changes to the bulk properties of the bioprosthetic valve, and reduce, minimize, or prevent negative patient outcomes due to the processing method. Furthermore, all materials used in this process (with the exception of pro-endothelial molecules) can be cheaply produced in very large quantities.

Further, another advantage of this method is that it results in a more consistent, even coating on the surface as compared to other methods. One of the major issues with surface modification of the bioprosthetic valves is that the surface is extremely heterogeneous with a very complex topography. This makes most traditional methods of hydrogel crosslinking (e.g. white light or UV light) difficult or impossible because the topography would cause inconsistent crosslinking across the surface. The glucose oxidase reaction is a creative way around this problem, because it depends on diffusion of glucose out of the tissue to initiate polymerization, a factor that will not vary significantly across the tissue surface. In fact, our preliminary results indicate that with this method we can get a very even coating on the surface, in spite of irregularities.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art, including combinations of aspects or features of the embodiments and examples disclosed herein. Such other examples are intended to be within the scope of the claims if they have structural elements that do not differ from the literal language of the claims, or if they include equivalent structural elements with insubstantial differences from the literal languages of the claims. The specific embodiments described above have been shown by way of example, and it should be understood that these embodiments may be susceptible to various modifications and alternative forms, including combinations of various features and aspects of the examples or embodiments discussed herein. It should be further understood that the claims are not intended to be limited to the particular forms disclosed, but rather to cover all modifications, equivalents, and alternatives falling within the spirit and scope of this disclosure.

The invention claimed is:

1. A method, comprising:
coating a surface of an implantable medical device with an anti-fouling coating, wherein the anti-fouling coating comprises a polyethylene-glycol (PEG)-based, hydrogel, wherein coating the surface of the implantable medical device comprises:
incubating the implantable medical device in a first solution to add one or more anchoring points on the surface of the implantable medical device, wherein the first solution comprises a bifunctional PEG macromer and glucose; and
incubating the implantable medical device having the one or more anchoring points in a second solution to form the anti-fouling coating, wherein the second solution comprises polyethylene glycol diacrylate (PEGDA) or polyethylene glycol diacrylamide (PEGDAA), glucose oxidase, and iron(II) ions.

2. The method of claim 1, wherein the one or more anchoring points each comprise an amine-reactive n-hydroxysuccinimide (NHS) linker, a PEG chain, and an acrylate group.

3. The method of claim 1, wherein the one or more anchoring points each comprise an amine-reactive n-hydroxysuccinimide (NHS) linker, a PEG chain, and a thiol group.

4. The method of claim 1, wherein the second solution comprises iron(II) sulfate heptahydrate comprising the iron (II) ions.

5. The method of claim 1, comprising washing the implantable medical device having the one or more anchoring points in phosphate buffered saline before incubating the implantable medical device having the one or more anchoring points in the second solution.

6. The method of claim 1, comprising adding one or more molecules to the second solution that are configured to promote endothelialization of the surface of the implantable medical device, wherein the one or more molecules comprise a peptide, a protein, an aptamer, or an antibody.

7. The method of claim 1, wherein the implantable medical device comprises a bioprosthetic valve.

8. The method of claim 1, wherein the anti-fouling coating is less than or equal to thirty micrometers thick.

9. A medical device, comprising:
a bioprosthetic valve comprising an anti-fouling coating covalently attached to a surface of the bioprosthetic valve, wherein the anti-fouling coating comprises a polyethylene-glycol (PEG)-based, hydrogel, wherein the bioprosthetic valve is prepared by a process for coating the surface of the bioprosthetic valve comprising:
incubating the bioprosthetic valve in a first solution to add one or more anchoring points on the surface of the bioprosthetic valve, wherein the first solution comprises a bifunctional PEG macromer and glucose; and
incubating the bioprosthetic valve having the one or more anchoring points in a second solution to form the anti-fouling coating, wherein the second solution comprises polyethylene glycol diacrylate (PEGDA) or polyethylene glycol diacrylamide (PEGDAA), glucose oxidase, and iron(II) ions.

10. The medical device of claim 9, wherein the anti-fouling coating comprises at least one molecule configured to promote endothelialization of the surface of the bioprosthetic valve, and wherein the at least one molecule comprises a peptide, a protein, an aptamer, or an antibody.

11. The medical device of claim 9, wherein the anti-fouling coating is less than or equal to thirty micrometers thick.

* * * * *